(12) United States Patent
Dosmann

(10) Patent No.: US 7,724,374 B2
(45) Date of Patent: May 25, 2010

(54) COAXIAL DIFFUSE REFLECTANCE READ HEAD

(75) Inventor: Andrew J. Dosmann, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 486 days.

(21) Appl. No.: 11/629,952

(22) PCT Filed: Jun. 16, 2005

(86) PCT No.: PCT/US2005/021230

§ 371 (c)(1),
(2), (4) Date: Dec. 15, 2006

(87) PCT Pub. No.: WO2006/009754

PCT Pub. Date: Jan. 26, 2006

(65) Prior Publication Data

US 2009/0021743 A1    Jan. 22, 2009

Related U.S. Application Data

(60) Provisional application No. 60/580,408, filed on Jun. 17, 2004.

(51) Int. Cl.
| | |
|---|---|
| G01N 21/47 | (2006.01) |
| G01J 1/04 | (2006.01) |
| G01J 1/42 | (2006.01) |
| G01J 5/08 | (2006.01) |
| G02B 6/00 | (2006.01) |
| A61B 6/00 | (2006.01) |

(52) U.S. Cl. .......... 356/446; 250/227.11; 385/12; 600/473; 600/476

(58) Field of Classification Search ............ None
See application file for complete search history.

(56) References Cited

U.S. PATENT DOCUMENTS

| | | | |
|---|---|---|---|
| 4,890,926 A | 1/1990 | Dosmann et al. | 356/369 |
| 4,922,919 A | 5/1990 | Novack | 128/633 |
| 5,096,671 A | 3/1992 | Kane et al. | 422/82.07 |
| 5,155,628 A | 10/1992 | Dosmann | 359/640 |

(Continued)

FOREIGN PATENT DOCUMENTS

JP    63239401 A  *  10/1988

(Continued)

OTHER PUBLICATIONS

Written Opinion of the International Searching Authority corresponding to co-pending International Patent Application No. PCT/US2005/021230, European Patent Office, dated Oct. 14, 2005, 7 pages.

(Continued)

*Primary Examiner*—Tarifur Chowdhury
*Assistant Examiner*—Gordon J Stock, Jr.
(74) *Attorney, Agent, or Firm*—Nixon Peabody LLP

(57) ABSTRACT

Improved performance in reflectance photometry is obtained by employing an optical fiber to direct collimated light to a test area and to return both diffuse and specular light from the test area. Specular light is prevented from reaching a light detector by a spatial filter, while diffuse light is collected and measured.

28 Claims, 3 Drawing Sheets

U.S. PATENT DOCUMENTS

| | | | | |
|---|---|---|---|---|
| 5,290,275 | A | 3/1994 | Kittrell et al. | 606/15 |
| 5,321,492 | A | 6/1994 | Detwiler et al. | 356/73 |
| 5,361,314 | A | 11/1994 | Kopelman et al. | 385/12 |
| 5,449,898 | A | 9/1995 | Dosmann | 250/208.1 |
| 5,477,326 | A | 12/1995 | Dosmann | 356/406 |
| 5,518,689 | A | 5/1996 | Dosmann et al. | 422/82.05 |
| 5,611,999 | A | 3/1997 | Dosmann et al. | 422/82.05 |
| 5,625,459 | A * | 4/1997 | Driver | 356/446 |
| 5,627,922 | A | 5/1997 | Kopelman et al. | 385/12 |
| 5,701,181 | A * | 12/1997 | Boiarski et al. | 356/446 |
| 5,713,364 | A * | 2/1998 | DeBaryshe et al. | 600/476 |
| 5,813,987 | A | 9/1998 | Modell et al. | 600/473 |
| 5,818,996 | A * | 10/1998 | Doyle | 385/115 |
| 6,157,472 | A | 12/2000 | Eum et al. | 359/18 |
| 6,181,417 | B1 | 1/2001 | Dosmann | 356/326 |
| 6,187,267 | B1 * | 2/2001 | Taylor et al. | 422/52 |
| 6,272,262 | B1 | 8/2001 | Kopelman et al. | 385/12 |
| 6,535,753 | B1 | 3/2003 | Raskas | 600/310 |
| 6,544,193 | B2 * | 4/2003 | Abreu | 600/558 |
| 6,563,992 | B1 * | 5/2003 | Doyle | 385/115 |
| 6,636,652 | B1 | 10/2003 | Kopelman et al. | 385/12 |
| 6,922,576 | B2 | 7/2005 | Raskas | 600/316 |
| 2001/0000129 | A1 | 4/2001 | Raskas | 356/39 |
| 2002/0171831 | A1 | 11/2002 | Backman et al. | 356/369 |
| 2003/0008408 | A1 * | 1/2003 | Colvin, Jr. | 436/166 |
| 2003/0210393 | A1 | 11/2003 | Vaez-Iravani et al. | 356/237.4 |
| 2004/0042001 | A1 | 3/2004 | Vaez-Iravani et al. | 356/237.2 |

FOREIGN PATENT DOCUMENTS

| | | |
|---|---|---|
| RU | 2006837 | 1/1994 |
| SU | 1368741 | 1/1988 |
| WO | WO 03/056378 A1 | 7/2003 |

OTHER PUBLICATIONS

International Search Report corresponding to co-pending International Patent Application No. PCT/US2005/021230, European Patent Office, dated Oct. 14, 2005, 4 pages.

* cited by examiner

COAXIAL DIFFUSE REFLECTANCE READ HEAD

CROSS-REFERENCE TO RELATED APPLICATIONS

This application claims priority to Application No. 60/580,408, filed Jun. 17, 2004, which is incorporated by reference in its entirety.

FIELD OF THE INVENTION

This invention relates to instruments used to measure the optical response to biological samples, such as those used to measure the glucose content of blood.

BACKGROUND OF THE INVENTION

Medical conditions are often diagnosed or monitored with the assistance of test strips that provide an optical response, (e.g., color) to reactions between analytes in a biological sample (e.g., glucose in whole blood) and reagents disposed on the test strip. Although an optical response can be read visually, frequently they are measured using reflectance photometry. In that method, light is directed onto a reagent-containing area on the test strip and light returned from the test area is detected and correlated with the amount of the analyte reacted on the test strip.

Many patents disclose arrangements of light sources and detectors intended to improve the performance of instruments employing reflectance photometry. Examples include U.S. Pat. Nos. 6,181,417; 5,611,999; 4,890,926; 5,155,628; 5,449,898 and 5,477,326. Typically, LEDs are used to provide a high intensity, narrow band width light source. Light returned from a test strip that has been affected by the optical properties of the test area, referred to as diffuse light, is collected and measured by a photo detector. Returning light, referred to as specular light herein, which is not affected by the test area, is prevented from reaching the light detector.

The light, as it travels between the light source and the light detector, has been handled with various methods familiar to those skilled in the art. Optical fibers have been employed in some methods. An example is found in U.S. Pat. No. 5,701,181 in which an LED supplies light through an optical fiber bundle at an angle of 30 degrees to a pad on a test strip. The reflected light is directed to a light detector via a bi-convex lens positioned behind a threaded light baffle to a second bundle of optical fibers.

Another sensing device of a completely different design is described in U.S. Pat. Nos. 6,157,472 and 6,535,753. It employs optical fibers in a self-contained unit to direct light into a very small sensing tip directly in contact with the subject being tested and to receive light reflected back from the tip. The sensing tip is extremely small and is intended to enter the skin of a patient with little or no sensation being felt. The tip is coated with materials that are selected to react with the analyte to be detected. An example given in U.S. Pat. No. 6,535,753 employs a glucose oxidase reagent system. Optical fibers tipped with reagents have been proposed for measuring other analytes, such as nitric oxide. Another example is found in U.S. Pat. No. 6,636,652.

Typical instruments have a number of limitations that relate to the handling of light. The amount of diffused light returned from the test area is small and therefore the test area must be relatively large, leading to larger equipment than would be desired. The arrangements of the optical elements of the instruments present problems for the designer. Further, eliminating specular light reflections, that is, light that has not been affected by the optical response of the test area, generally is not completely successful. Consequently, further improvements in such instruments are continually sought. The present invention employs fiber optics to overcome limitations found in conventional instruments, as will be seen in the description below.

SUMMARY OF THE INVENTION

In one embodiment, the invention is a coaxial diffuse reflectance read head providing improved performance in reflectance photometry used to measure the optical response to reactions between analytes in biological samples (e.g., glucose in whole blood) and appropriate reagents on a test strip. The same optical fiber is used coaxially, that is, to transmit collimated light to a testing area and to return both diffuse and specular light. A beam splitter directs collimated light from a light source into the optical fiber and directs the specular light received from the testing area to a spatial filter, which is positioned to block access of the specular light to the light detector. The diffuse light passes around the spatial filter, is measured by the light detector, and then correlated with the amount of an analyte reacted in the testing area. In one preferred embodiment, the edges of the beam splitter are beveled, preferably at an angle of 45 degrees, to limit the loss of diffuse reflected light compared with a beam splitter having 90 degree edges.

In another aspect, the invention is a method of measuring diffuse light returned from a test area exposed to a light source. Collimated light is directed via a beam splitter and an optical fiber to a testing area. The optical fiber is either in contact with the testing area or closely approaches the testing area. Both diffuse and specular light are returned from the testing area via the optical fiber to the beam splitter. Specular light passing through the beam splitter is directed to an opaque area that serves as a spatial filter, while the diffuse light passes around the spatial filter to a light detector.

In another embodiment, the invention is a coaxial reflectance read head that improves performance of optical fiber sensors coated with reagents for direct contact with a sample. The optical fiber tip replaces the test strips used with the embodiment described above. The light directed to the fiber tip and the sample is returned to a light detector by the optical fiber. The specular light is passed through a beam splitter and blocked from entering the light detector by an opaque area that serves as a spatial filter, while the diffuse light containing information about the optical response of the sample passes around the opaque area onto the light detector.

DESCRIPTION OF THE PREFERRED EMBODIMENTS

Figure 1:
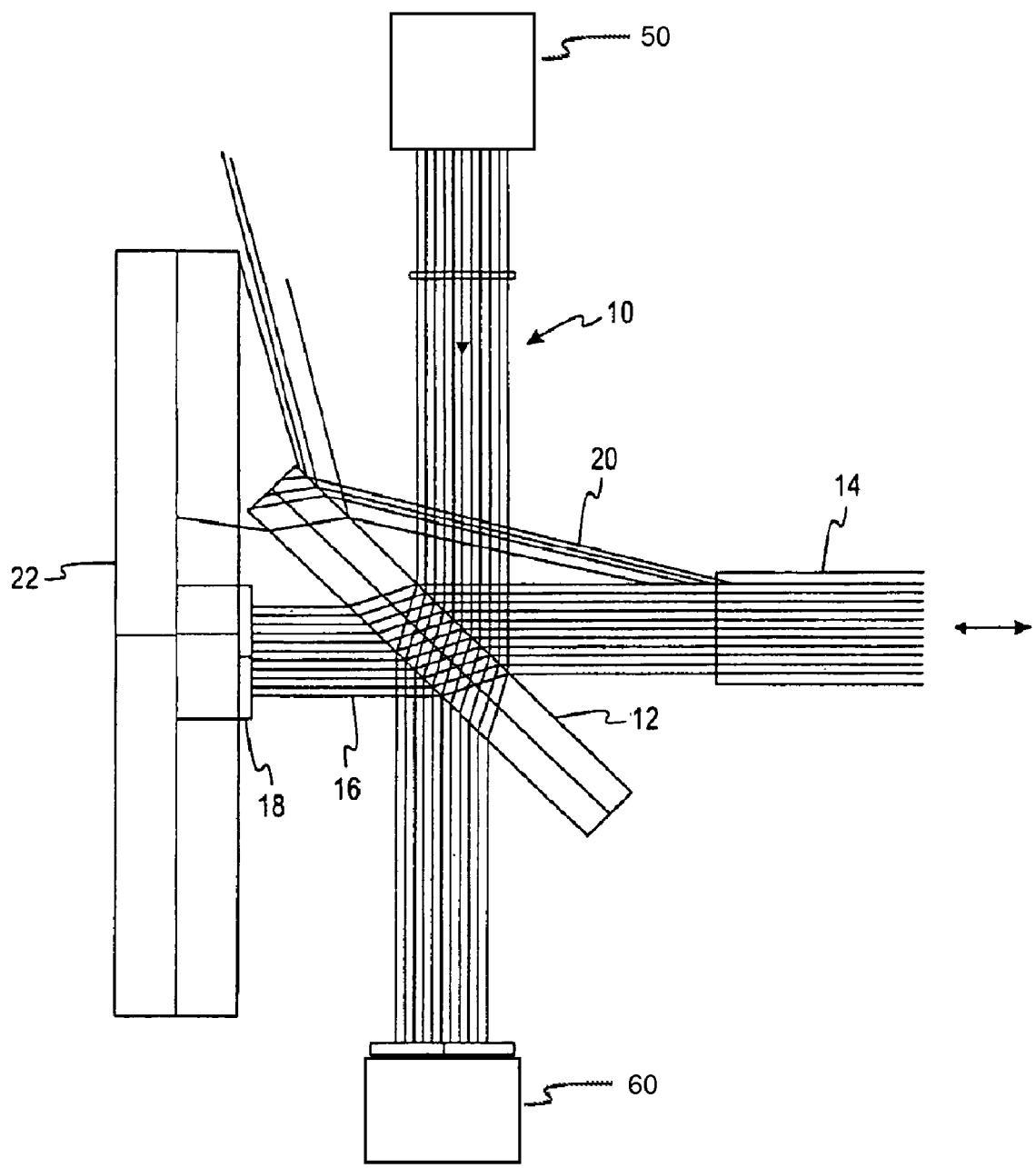
FIG. 1 is a schematic diagram of the optics of the invention.

The reagent strips that are used in clinical chemistry to determine the presence or absence of certain markers for disease generally develop an optical response (e.g., change color) in response to the presence of an analyte of interest in the sample applied to the reagent strip. The optical response of the test strip may be read with reference to color charts and the like, but instruments are commonly used to more accurately measure the optical response. Measuring the glucose content in whole blood is particularly important, but other analytes such as protein, blood, ketones, bilirubin, urobilinogen, nitrite, cholesterol, etc. may be tested in a similar manner.

In such instruments, a light source supplies light to a test area and the light returned from the surface is measured and related to the amount of the analyte that was reacted on the test strip. The returning light may be divided into two types. First, light that is only returned from the test area without being affected by the change in color (or other optical response) that has occurred on the test area. Such light is referred to as "specular light." The specular light is "noise" and therefore should not reach the light detector used to measure the second type of light, which is referred to as "diffuse light." Diffuse light is understood to have been affected by the test area so that it is representative of the optical response of the sample to reagents in the test area. Thus the diffuse light provides a measure of the amount of the analyte present in the test area. For example, the incident light may be absorbed at wavelengths corresponding to the color that was developed, making the diffused light deficient in those wavelengths in proportion to the amount of the analyte.

In instruments such as those described in the patents mentioned earlier, various arrangements of the optic elements are used to limit the access of the specular light to the light detector and to recover the maximum amount of diffuse light, so that the measurement of the diffuse light is as accurate as possible. Typically, LEDs or other light sources are used. The light source and its associated optics, the test area, and the light detector are positioned to limit the recovery of specular light and maximize the recovery of diffuse light. The present invention provides improved performance while at the same time making it possible to reduce the size of the read head and overcome the mechanical limitations characteristic of the previous designs.

The invention reduces the size of the test area compared to designs of the prior art by transmitting light to and from the test area via a single optical fiber that is close to or actually in contact with the test area. In a preferred embodiment, the optical fiber is about 1 mm in diameter. Since the optical fiber is so small and flexible it is possible to locate the remainder of the optical parts without concern about loss of light that previously dictated the close proximity of the light source, the test area and the light detector. Also, the need for close mechanical tolerances in the manufacture of the read head is reduced. Finally, the diffuse light leaving the test area is collected from the entire area, which has not been easily accomplished when the light is directed through a lens or other optical features into a light detector located some distance from the test area.

Figure 2:
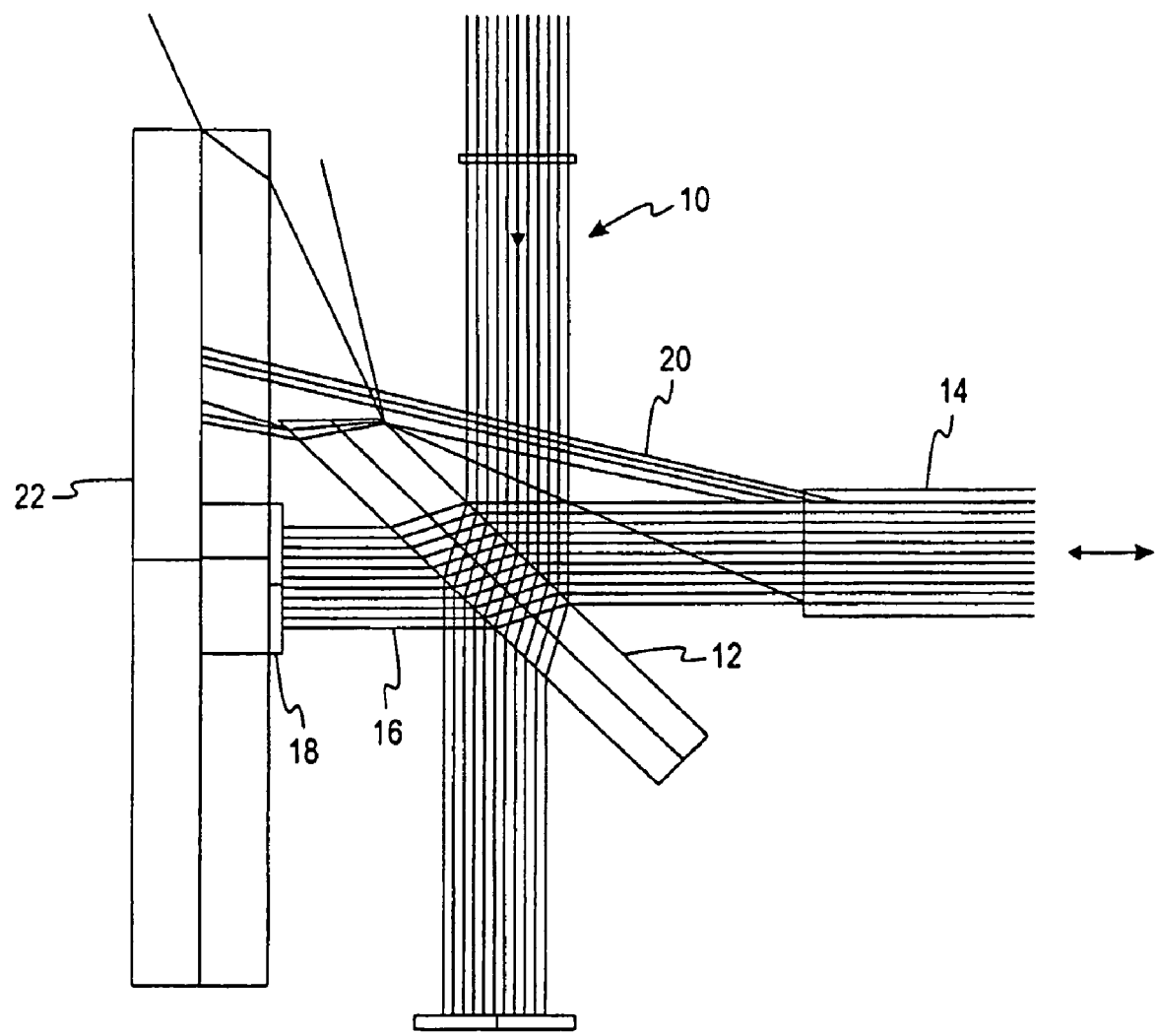
FIG. 2 is a schematic diagram of preferred optics of the invention.

FIG. 1 provides a schematic illustration of the principal features of the invention. Collimated light 10, provided by, for example, an LED (or other light source 50) and a collimating lens, is directed to a beam splitter 12 positioned at a 45 degree angle to the column of light. Beam splitters are familiar to those skilled in the optical arts. They are able to pass a portion of the light they receive to a reference detector 60 which provides a means to correct variations in the intensity of illumination light that occur over a period of use. The remainder of the light is reflected from the beam splitter into the test area. In one embodiment of the present invention, the reflected light is directed to an optical fiber 14 located close to the beam splitter, preferably about 2 mm from the surface. The light passes through the optical fiber until it reaches the test area (not shown). Since the optical fiber is substantially the same size as the testing area, all of the collimated light is received by the test area. The light leaving the test area is returned through the same optical fiber 14. The specular light is considered to be merely reflected and not affected by the color or other optical response developed by the reactions that had occurred on the test area. The diffuse light has been affected by the optical response that occurs in the test area and contains the information needed to determine the amount of an analyte that had reacted at the test area. Both types of light return through the optical fiber. When they reach the beam splitter, the specular light 16 is considered to be light that remains collimated and passes through the beam splitter. The specular light is refracted by the material used in the beam splitter 12 as shown in FIGS. 1 and 2. The specular light is blocked from entering the light detector 22 by an opaque area that serves as a spatial filter 18. The diffuse light 20 is considered to be the light that spreads out as it leaves the optical fiber 14 and passes through and around the beam splitter 12 as shown and reaches the light detector 22. The diffuse light reaching the light detector is convened to an electrical signal that is correlated by an algorithm to indicate the amount of the analyte reacted at the test area.

It will be seen from the FIG. 1 that a portion of the diffuse light is lost, since it passes by the light detector and some diffuse light does not pass through the beam splitter at its edge. In a similar, but preferred embodiment illustrated in FIG. 2, more of the diffuse light is captured and measured by the light detector. In that embodiment, the outer edges of the beam splitter 12 are beveled, exemplified by the 45 degree angle shown in FIG. 2 to reduce the loss of the diffuse light. The preferred angle may be varied depending on the optical properties of the beam splitter, the position of the end of the optical fiber relative to the beam splitter, and other factors related to the relative position of the optical elements in the read head.

In specific examples of the invention, the light source is an LED producing a narrow bandwidth of light having center wavelengths in the range of about 400 nm to about 1,000 nm, which is collimated by a collimation lens. The light source and associated optics are located about 3 mm from the beam splitter, which may be one of several types known in the art, preferably, a 50/50 plate beam splitter. The beam splitter has a thickness of about 0.5 mm, a length of about 9 mm, and a width of about 3.5 mm. The diameter of the collimated light is smaller than the diameter of the optical fiber. For example, a 0.75 mm diameter beam compared to a 1 mm diameter fiber, although the diameter of the collimated light and optical fiber may be varied as desired to correspond to the size of the test area to be read. Typical diameters are expected to be in the range of about 0.25 to 3 mm. The optical fiber is positioned close to the sample test area to limit the loss of the returning light. Preferably, the distance will be in the range of 0.25 mm to 2.0 mm. As previously mentioned, it is a feature of this invention that the optical fiber allows separation of the test area from the associated illumination and detection optics in a manner not possible with typical instrument lacking an optical fiber. If the optical fiber is intended to be disposable after each use, the length will generally be short, for example from about 5 to about 15 mm. However, the fiber can be longer if replacement after each use is not required. Specular and diffuse light returning via the optical fiber will pass though the beam splitter, which will be positioned from about 1 to about 2 mm from the spatial filter. The spatial filter blocks the specular light, and is located directly in front of the light detector. The width of the spatial filter and light detector is from about 0.5 to about 3.5 mm, and the opaque area that blocks the specular light generally will be larger than the diameter of the optical fiber. For example, if the optical fiber has a diameter of 1 mm, then the opaque portion of the spatial filter will be about 1.4 mm to assure that all of the specular light is blocked. It will be evident to one skilled in the optical arts that the size and positioning of the optical elements may be varied without departing from the general description of the invention. For example, if the collimated beam diameter is 2 mm, then the fiber diameter would be 2.5 mm, and the spatial filter diameter would be 3.0 mm.

Figure 3:
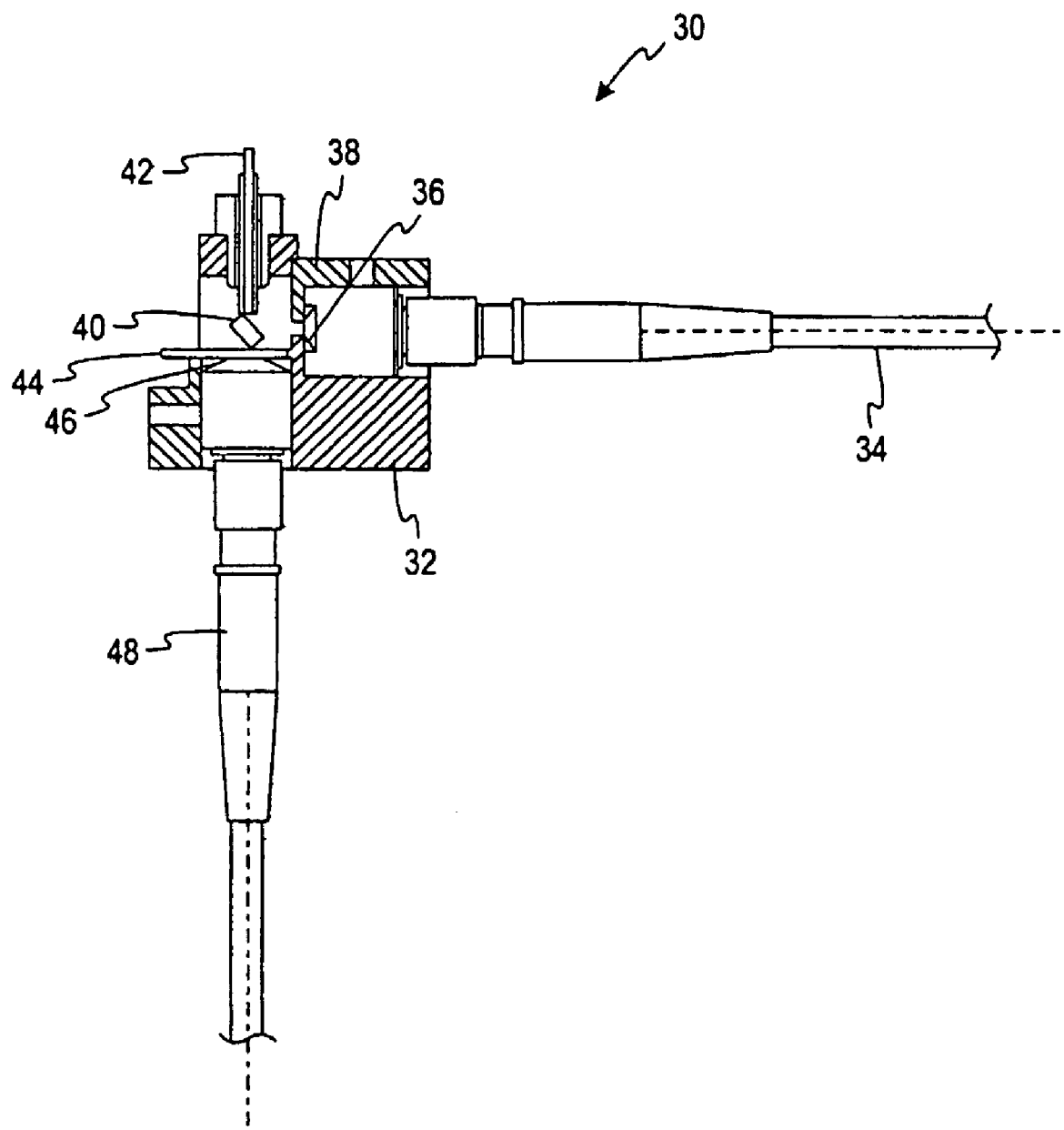
FIG. 3 is a cross-sectional view of a read head of the invention.

FIG. 3 shows, in a cross-sectional view, a configuration of the read head 30 of the invention in which the light source and light detector are not integral with the read head. The body 32 of the read head 30 may be of various materials and, typically, black ABS resin will be used. The principal design considerations other than structural integrity are that the body 32 is black to reduce stray light cross talk between the illumination and detection channels. As discussed previously, the read head need not be close to the test area, as has been the case with previous designs. The light to illuminate the test area can be supplied by an LED or a white light source such as a halogen lamp. In this example, the light enters through an optical fiber 34 and is collimated by a lens system 36. The collimated light is passed through an aperture 38, and is directed to the beam splitter 40, which passes a fraction of the light to a reference light detector (not shown) aligned with the direction of the collimated light. The remaining light is directed at a 45° angle into the optical fiber 42 that transmits the light to the test area (not shown). Diffuse and specular light returns from the test area via the optical fiber 42 to the beam splitter 40, which directs the returning light to the spatial filter 44 and a lens 46 that focuses the diffuse light onto an optical fiber 48, leading to the light detector (not shown). It will be evident to those skilled in the art that in alternative embodiments an LED light source could be close-coupled to the read head and the light detector also positioned close to the read head.

Two alternative embodiments relate to the positioning of the end of the optical fiber relative to the test area. In the first, the end of the optical fiber is located close to, but not in contact with the test area, which contains reagents for reaction with analytes in the sample. For example, the fiber may be from about 0.05 to about 0.25 mm from the surface of the test area, so that the fiber receives as much of the reflected light as possible, but the risk of contamination is minimized. In such an embodiment, the fiber may be used for many tests without needing replacement, since it is the test area that is used once and discarded. That is, the test area corresponds to the test strips containing reagents in which a liquid sample is placed and reacted.

In the second embodiment, the fiber is in direct contact with the sample in the test area. In contrast with the first embodiment, the sample is not added to the test area to contact reagents previously placed there, such as the test strips used in measuring glucose in blood. Instead, the optical fiber tip carries the reagents needed to react with the analyte (e.g., glucose) in the sample. When the fiber tip touches the sample, the necessary reactions occur and optical response is obtained. Collimated light enters the interface between the optical fiber tip and the sample and reflected light is returned via the fiber to the light detector as in the first embodiment. Since the end of the optical fiber becomes in effect the test strip, the optical fiber would be replaced after each use.

In either embodiment, the instrument could be programmed to begin monitoring the light leaving the test area after the test strip or the sample is in place. A sudden drop in light returning from the test area is an indication of the start of the reaction between the sample and the reagents, which can be used to determine an accurate start time for the assay. Performance improvements and reduction in test time are improved by knowing the exact start time of an assay.

The invention may be employed in determining many analytes. For example, in one embodiment of the present invention, the test area may contain reagents adapted to the determination of glucose, such as the enzyme glucose oxidase in combination with indicators such as tetramethylbenzidine or dianisidine or 4-aminoantipyrine plus p-hydroxybenzenesulfonate in the presence of peroxidase. Alternatively, the enzyme glucose dehydrogenase could be used in combination with tetrazolium indicators such as p-iodonitrotetrazolium violet (INT), nitroblue tetrazolium (NBT), or tetranitroblue tetrazolium (TNBT).

For determining the cholesterol in a blood sample, the test area may contain the enzymes cholesterol ester hydrolase and cholesterol oxidase plus indicators such as tetramethylbenzidine or dianisidine or 4-aminoantipyrine plus p-hydroxybenzenesulfonate in the presence of peroxidase.

For determining tryglycerides, the enzymes lipase, glycerokinase, glycerolphosphate dehydrogenase and diaphorase in combination with tetrazolium indicators such as p-iodonitrotetrazolium violet (INT), nitroblue tetrazolium (NBT), or tetranitroblue tetrazolium (TNBT) will produce a color indicative of the tryglyceride levels. The enzymes lipase, glycerokinase, glycerol phosphate oxidase combined with indicators such as tetramethylbenzidine or dianisidine or 4-aminoantipyrine plus p-hydroxybenzenesulfonate in the presence of peroxidase also will produce color in response to triglycerides.

A test sensitive to the enzyme amylase can be made from the enzyme alpha glucosidase and the chromogenic indicator 4,6-ethylidene (G7) nitrophenyl (G1)-(alpha) D-maltoheptoside. Hemoglobin can be detected by potassium ferricyanide, potassium cyanide and sodium bicarbonate where the hemoglobin is converted to methemoglobin.

When the tip of the optical fiber serves as a carrier for the reagents, that is, becomes the equivalent of a test strip, the principal reagents will be substantially the same as those used in test strips, although the formulations may be modified as required for application to the end of an optical fiber.

What is claimed is:

1. A coaxial read head comprising:
   (a) a collimated light source;
   (b) a beam splitter adapted to receive collimated light from said collimated light source and adapted to direct a portion of said collimated light to an optical fiber;
   (c) an optical fiber adapted to direct said collimated light received from said beam splitter at one end of said optical fiber to a test area at a second end of said optical fiber and adapted to direct specular and diffuse light from said test area to said beam splitter, said optical fiber being either in contact with said test area or closely approaching said test area; and
   (d) a spatial filter adapted to receive said specular light from said beam splitter and to block access of said specular light to a light detector.

2. The coaxial read head of claim 1, further comprising a light detector disposed behind said spatial filter adapted to receive diffuse light from said beam splitter and to produce an electrical signal from said diffuse light.

3. The coaxial read head of claim 1 further comprising a reference light detector for receiving a second portion of said collimated light, said second portion of collimated light passing through said beam splitter.

4. The coaxial read head of claim 1 wherein said collimated light source comprises an LED.

5. The coaxial read head of claim 1 wherein said collimated light source is a halogen lamp.

6. The coaxial read head of claim 1 wherein said beam splitter is a 50/50 beam splitter.

7. The coaxial read head of claim 1 wherein said optical fiber has a diameter larger than the diameter of said collimated light.

8. The coaxial read head of claim 1, wherein said specular and diffuse light are reflected light from said test area.

9. The coaxial read head of claim 1 wherein said beam splitter has outer edges beveled to reduce loss of diffuse light received from said optical fiber.

10. The coaxial read head of claim 1 wherein said spatial filter contains an opaque area disposed to block specular light passing through said beam splitter.

11. The coaxial read head of claim 1 wherein said optical fiber has a diameter substantially equal to said test area.

12. The coaxial read head of claim 1 wherein said optical fiber has a reagent coating on said second end of the fiber and said fiber is positioned to contact a sample on said test area.

13. The coaxial read head of claim 9 wherein said beam splitter has outer edges beveled at a 45° angle.

14. The coaxial read head of claim 10 wherein said opaque area is larger than said optical fiber.

15. The coaxial read head of claim 11 wherein said optical fiber and said test area have diameters in a range from about 0.25 to 3 mm.

16. The coaxial read head of claim 15 wherein said optical fiber has a diameter of 1 mm.

17. The coaxial read head of claim 12 wherein said test area contains a test strip containing reagents for reacting with a sample in said test strip.

18. The coaxial read head of claim 12 wherein said optical fiber is disposable.

19. The coaxial read head of claim 18 wherein said optical fiber is positioned 0.25 to 2 mm from said test area.

20. A method of measuring an analyte in a biological sample the method comprising the acts of:

(a) providing collimated light from a light source;
(b) directing said collimated light with a beam splitter into a first end of an optical fiber, a second end of said optical fiber being in contact with a test area or closely approaching said test area;
(c) directing diffuse and specular light from said test area via said optical fiber to said beam splitter, said specular light passing through said beam splitter and contacting a spatial filter, thereby preventing said specular light from being detected, said diffuse light passing around said spatial filter and contacting a light detector; and
(d) measuring the diffuse light with said light detector and correlating the measured diffuse light with the amount of an analyte in said biological sample.

21. The method of claim 20 wherein said optical fiber has a diameter substantially equal to said test area.

22. The method of claim 20 wherein said beam splitter has outer edges beveled to reduce loss of diffuse light received from said optical fiber.

23. The method of claim 20 wherein said optical fiber has a reagent coating on said second end of said optical fiber and said fiber is positioned to contact said sample on said test area.

24. The method of claim 20 wherein said test area is monitored for an initial change in diffuse light, said change in diffuse light being used as an indicator for the beginning of a reaction with said analyte in said test area.

25. The method of claim 20 wherein said analyte is glucose and said biological sample is whole blood.

26. The method of claim 20, wherein said specular and diffuse light are reflected light from said test area.

27. The method of claim 20 wherein said optical fiber is positioned to closely approach said test area and to minimize loss of said collimated light.

28. The method of claim 27 wherein said optical fiber supplies collimated light to a test strip in said test area.

* * * * *